United States Patent [19]

Lundquist

[11] 4,055,176
[45] Oct. 25, 1977

[54] UNIVERSAL DRIP CHAMBER AND SPIKE ASSEMBLY

[75] Inventor: Ingemar H. Lundquist, Oakland, Calif.

[73] Assignee: Valleylab, Boulder, Colo.

[21] Appl. No.: 689,114

[22] Filed: May 24, 1976

[51] Int. Cl.² .............................................. A61M 5/16
[52] U.S. Cl. .................. 128/214 C; 137/399
[58] Field of Search ........................ 128/214 C, 214.2; 73/198; 137/399

[56] References Cited

U.S. PATENT DOCUMENTS

| 2,672,051 | 3/1954 | Butler | 128/214 C X |
| 2,879,784 | 3/1959 | Cutter | 128/214 C X |
| 3,092,106 | 6/1963 | Butler | 128/214 C |
| 3,316,908 | 5/1967 | Burke | 128/214 C |
| 3,465,784 | 9/1969 | Cofoid | 128/214 C X |
| 3,521,635 | 6/1970 | Koehn | 128/214 C |

FOREIGN PATENT DOCUMENTS 2,023,366  12/1971  Germany .......................... 128/214 C Primary Examiner—Dalton L. Truluck
Attorney, Agent, or Firm—Flehr, Hohbach, Test, Albritton & Herbert

[57] ABSTRACT

Universal drip chamber and spike assembly for use with a source of intravenous liquid contained in a bottle having a neck with a permeable stopper disposed in the neck and for use with a tube adapted to be connected to a patient. The Universal drip chamber comprises a body defining the upper portion of a drip chamber. The drip chamber body has a relatively rigid substantially transparent wall surrounding the upper portion of the chamber and being open at its lower end. A drip chamber booth formed of a flexible rubber-like material is secured to the lower end of the said drip chamber body and defines the lower portion of the drip chamber. The booth has an outlet flow passage extending through the lower extremity of the same and is in communication with the drip chamber. The booth has means forming a valve seat in the lower portion of the drip chamber surrounding the outlet flow passage. A ball capable of floating in said liquid is disposed in said drip chamber and is capable of engaging said valve seat to prevent the flow of liquid from said drip chamber through the outlet flow passage in said booth. The booth is sufficiently compliant so that it can be squeezed by hand to dislodge the ball from the valve seat. The booth has sufficient length above the seat so that when the ball is disposed in the seat, the booth can be squeezed by hand without lodging the ball to pump liquid into the drip chamber. The spike assembly has a first flow passage therein in communication with the drip chamber whereby when the spike is completely inserted into the stopper in the bottle, fluid can pass from the bottle into the drip chamber. The spike assembly is provided with first and second steps with the second step being closer to outer end of the spike assembly than the first step. The first flow passage opens through the first step. The spike assembly is provided with a second flow of passage which is formed in the spike assembly and has one end opening through the second step and has the other end open to the atmosphere. Hydrophobic air filter means is disposed in the second flow passage so that air passing from the atmosphere and through said second passage must pass through the hydrophobic filter.

7 Claims, 5 Drawing Figures

UNIVERSAL DRIP CHAMBER AND SPIKE ASSEMBLY

BACKGROUND OF THE INVENTION

In the past many different types of drip chambers have been provided. Also spike assemblies have been provided for use with such drip chambers. Different types of spike assemblies have been provided because of the different types of intravenous fluid bottles which are utilized. Some bottles are collapsible, others have their own indepedent standpipes, and others need means in the spike assembly for venting the bottle to atmosphere. Filters also have been provided for filtering the air which is introduced into the bottles. All of these various pieces of apparatus have disadvantages. In addition, they are not universally adaptable to other types of i.v. bottles. There is, therefore, a need for a universal drip chamber and spike assembly which can be utilized with various types of i.v. bottles.

OBJECTS AND SUMMARY OF THE INVENTION

The universal drip chamber and spike assembly is for use with a source of i.v. fluid contained in a bottle having a neck with a permeable stopper disposed in the neck. It is also for use with a tube adapted to be connected to a patient. The universal drip chamber and spike assembly consists of a drip chamber body defining the upper portion of the drip chamber. The body has a substantially transparent wall surrounding the upper portion of the drip chamber and is open at the lower end. A drip chamber booth formed of a flexible rubber-like material is secured to the lower end of the drip chamber body and defines the lower portion of the drip chamber. The booth has an outlet flow passage extending through the lower extremity of the same which is in communication with the drip chamber. The booth is provided with means forming a valve seat within the drip chamber and surrounding the outlet flow passage. A ball-like valve member capable of floating in the liquid in said drip chamber is provided for engaging the valve seat for preventing the flow of liquid from the drip chamber through the outlet flow passage. The booth is sufficiently compliant so that it can be squeezed by hand to dislodge the ball-like valve member from the valve seat. The booth has sufficient length above the seat so that when the ball is disposed in the seat it can be squeezed by hand without dislodging the ball to pump liquid into the drip chamber. A spike assembly is mounted on the drip chamber body. The spike assembly is adapted to be inserted into the permeable stopper of the bottle. The spike assembly is adapted to be inserted into the permeable stopper of the bottle. The spike assembly is provided with a first flow passage therein which is in communication with the drip chamber whereby when said spike is inserted into said stopper, liquid can pass from said bottle into said drip chamber. The spike assembly is also provided with first and second steps with the second step being closer to the outer end of the spike assembly than the first step. The first flow passage opens through the first step. A second flow passage is provided in a spike assembly which opens through the second step and which is also open to the atmosphere. Hydrophobic air filter means is disposed in the second flow passage so that air passing from the atmosphere through said second flow passage must pass through the hydrophobic filter.

In general, it is an object of the present invention to provide universal drip chamber and spike assembly which can be utilized with various types of i.v. bottles.

Another object of the present invention is to provide universal drip chamber and spike assembly of the above character in which any air vented into the bottle through the spike assembly is filtered.

Another object of the present invention is to provide a universal drip chamber and spike assembly of the above character having a valve member which can readily be seated when the i.v. bottle is empty of liquid.

Another object of the present invention is to provide a universal drip chamber and spike assembly of the above character in which the drip chamber can be pumped by hand to fill the same from the i.v. bottle without dislodging the valve member from the valve seat.

Another object of the present invention is to provide a universal drip chamber and spike assembly of the above character which can be readily used by nurses and the like.

Another object of the present invention is to provide a universal drip chamber and spike assembly of the above character in which a new i.v. bottle can be inserted onto the spike assembly without the necessity of disconnecting the tube from the patient or without any danger of air getting into the tube leading to the patient.

Another object of the present invention is to provide a universal drip chamber and spike assembly of the above character in which the filter utilized is shielded from water and the like.

Another object of the present invention is to provide a universal drip chamber and spike assembly of the above character in which means is provided so that the valve member cannot close off the passage leading from the drip chamber into the i.v. bottle so that liquid can pass in both directions between the i.v. bottle and the drip chamber.

Additional objects and features of the invention will appear from the following description in which the preferred embodiment is set forth in conjunction with the accompanying drawings.

DESCRIPTION OF THE PREFERRED EMBODIMENT

Figure 1:
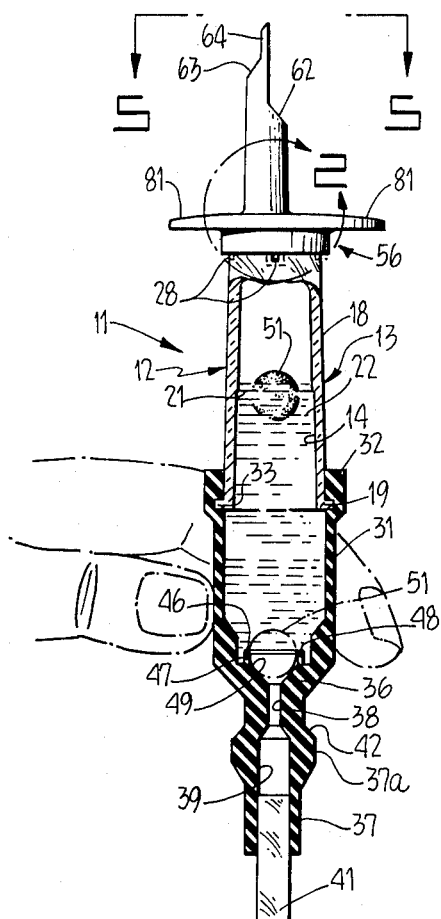
FIG. 1 is a side elevational view partially in cross section of a universal drip chamber and spike assembly incorporating the present invention.

The universal drip chamber and spike assembly 11 incorporating the present invention is shown in FIG. 1. As shown therein, it consists of a drip chamber body 12 and a drip chamber booth 13, both of which together define a drip chamber 14. A spike assembly 16 is mounted on the drip chamber body 12.

The universal drip chamber and spike assembly 11 is adapted to be utilized for introducing an intravenous liquid into the veins of a patient from a bottle containing the intravenous liquid. In addition, the universal drip chamber and spike assembly 11 is adapted to be utilized in conjunction with a control and pump of the type shown and described in the co-pending application, Ser. No. filed The universal drip chamber body 12 is formed of a suitable relatively rigid substantially transparent material such as a clear plastic. It has a generally cylindrical configuration with a slight taper inwardly in an upward direction. It is provided with a generally vertical wall 18 which surrounds the upper portion of the drip chamber 14. The lower end of the drip chamber body is open as shown. The lower extremity of the wall 18 is provided with an outwardly extending flange 19. A line 21 is formed on the wall 18 and serves as an indication as the desired uppermost level to which i.v. liquid 22 should rise in the drip chamber.

The drip chamber is also provided with a top wall 23 which extends substantially at right angles to the wall 18 and adjoins the wall 18. The wall 23 is provided with a centrally disposed opening 24 and is provided with an upper extending rim 26 which surrounds the opening 24. A plurality of upwardly extending circumferentially spaced slots 28 are provided in the upper extremity of the wall 18 which serve as air passages as hereinafter described.

The drip chamber booth 13 is formed of a suitable resilient material such as natural rubber of medical quality. It is translucent and has a suitable durometer such as 25 to 30, but the durometer may range from 20 to 40.

The drip chamber booth has a generally funnel-like configuration and has an upper cylindrical wall 31 which surrounds the lower portion of the drip chamber 14. A circular collar 32 is formed cylindrical with the wall 31. It is provided with an internal annular recess 33 which is adapted to receive the flange 19 of the drip chamber body 12 when the collar 32 is slipped over the lower extremity of the drip chamber body 12. The lower portion 36 of the drip chamber booth is generally conical as shown and is formed identical with the lower extremity of the wall 31. It is also formed identical with a tubular extension 37 which depends downly from the drip chamber 14. An outlet flow passage 38 is formed in the tubular extension 37 and extends from the drip chamber 14 with which it is in communication and into a larger bore 39 also formed in the tubular extension 37. The larger bore 39 is adapted to receive a flexible tube 41 which is adapted to be connected to a patient to supply intraveneous liquid to a patient. The tubular extension is provided with an enlarged portion 37a which has a tapered inclined surface 42 that can serve as an injection site for a hypodermic needle and the like when it is desired to introduce additional medication into the patient.

A valve seat 46 is formed in the drip chamber booth in the chamber 14 and encircles the outlet flow passage 38. It can be seen from FIG. 1 that the valve seat is in the form of an annulus 47 extending vertically and upwardly into the drip chamber 14 and is formed of the same material as the drip chamber booth. The upper extremity of the annulus 47 is provided with a taper so that there is formed an outwardly and upwardly inclined tapered surface 48. Valve seat 46 also includes a conical recess 49 formed within the annulus 47 which leads downwardly into the outlet flow passage 38.

The drip chamber booth 13 is formed of a relatively soft rubber as, for example, the 25 to 30 durometer rubber previously identified. It is desirable to utilize the relatively soft rubber because this makes the annulus 47 very flexible so that it can readily receive therein a spherical or ball-like valve member 51 as shown in FIG. 1. The ball-like valve member 51 is formed of a suitable material so that it will float in the i.v. liquid which is to be administered through the universal drip chamber and spike assembly 11. One material found to be satisfactory is a low density polyethelene having a specific gravity of approximately 0.091. The sphericity should be within 0.001 of an inch. The ball-like member 51 has a size which is only slightly greater than the inner diameter of the annulus 47. The annulus 47 is relatively thin, as for example within 10 to 15 thousandths of an inch so that it can be easily stretched to accommodate the ball to form an excellent seal between the valve seal and the ball 51 so as to prevent air from passing into the flow passage 38 when the ball 51 is within the seat. The inner tapered surface 48 provided on the annulus 47 also makes it easier for the ball to seat within the valve seat 46. Because the thin annulus 47 is very flexible, it is easy for the annulus to accommodate the ball and to form an air-tight seal with respect to the ball.

Figure 5:
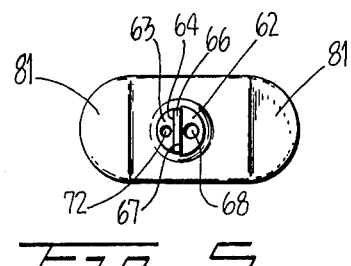
FIG. 5 is a top plan view looking along the line 5—5 of FIG. 1.

The spike assembly 16 is formed in one piece and is formed of a suitable material such as a clear plastic. It consists of a cap 56 which is formed by a planar top wall 57 and a cylindrical depending sidewall 58. A spike 61 is formed integrally with the cap 56. The spike 61 is generally tapered inwardly in an upward direction so that it has a shape of a truncated cone. It is provided with first and second steps 62 and 63 with the second step 63 being closer to the outer end of the spike 61 than the first step 62. The step 62 and 63 extend inwardly so that the central upper end portion or tip 64 of the spike is relatively narrow as can be seen from FIGS. 1 and 5. In addition, the tip 64 is provided with surfaces 66 and 67 which are included outwardly and downwardly from the center and which also incline towards one side so that the central portion of the spike 61 presents a relatively sharp point which can be readily inserted into the permeable member in the form of a cork which is provided in the neck of the i.v. bottle. As is well known to those skilled in the art, such corks are generally formed of a suitable permeable material such as rubber.

Figure 2:
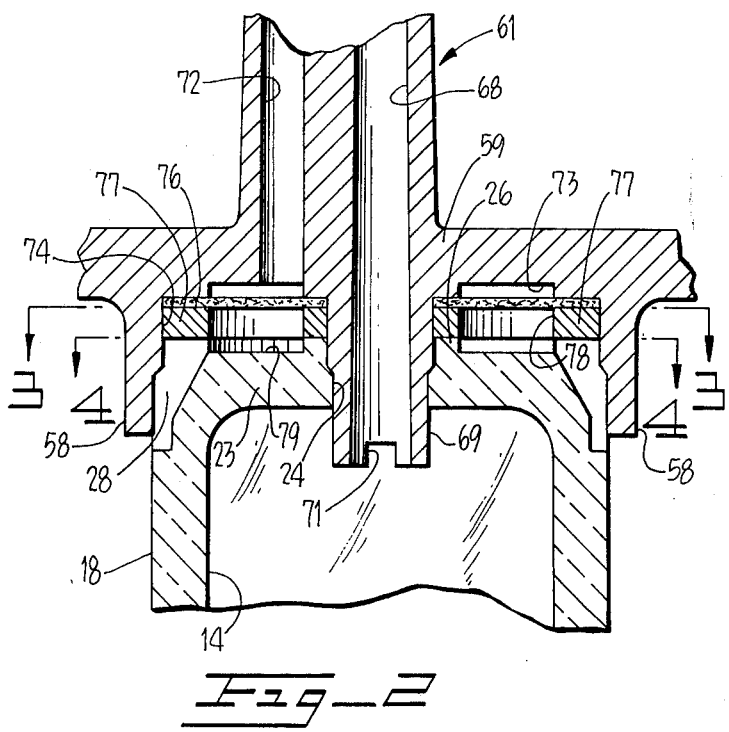
FIG. 2 is an enlarged cross sectional view of a portion of the spike assembly and drip chamber encircled by the line 2—2 in FIG. 1.
Figure 3:
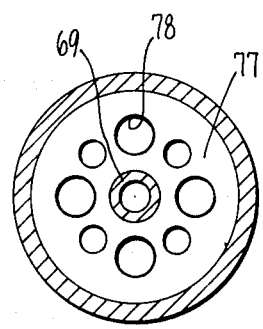
FIG. 3 is a cross sectional view taken along the line 3—3 of FIG. 2.
Figure 4:
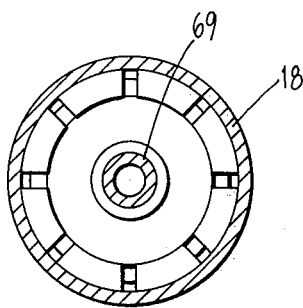
FIG. 4 is a cross sectional view taken along the line 4—4 of FIG. 2.

The spike 61 is formed with a first flow passage 68 which extends upwardly through the first step 62 and which also extends downwardly through the cap 56 and through an inner stem 69 formed integral with the cap 5.6. The stem 69 is positioned so that when the cap 56 is seated over the top of the drip chamber body 12 as shown in FIG. 2, it will seat within the opening 24 provided in the drip chamber body 12. As it will be noted, the lower extremity of the stem 69 is provided with rectangular cutouts 71 so that the flow passage 68 will not be occluded by the ball 51 in the event the ball 51 comes into engagement with the lower extremity of the stem 69 in the float chamber 14.

The spike 61 is also provided with a second flow passage 72 which opens upwardly through the second step 63 and which extends downwardly and opens into an annular recess 73 provided within the interior of the cap 56 and in the inside surface of the wall 57. The interior of the cap 56 is provided with another annular recess 74 which is larger in diameter than the recess 73 and has mounted therein a filter washer 76 formed of a suitable material such as "Gore-Tex" 0.2 μm filter material that is laminated onto a layer of polypropylene. The polyproplene provides a more stable support to make the filter washer 76 easier to handle. The filter washer serves as a hydrophobic filter. This filter washer 76 is mounted in the recess 74 and is supported therein by a filter support washer 77 formed of a suitable material such as a clear plastic. As can be seen, the filter support washer 77 is provided with a plurality of openings 78 which are spaced circumferentially around the central portion of the filter washer. As can be seen, the filter washer 77 also seats upon the rim 26 provided on the top of the drip chamber body 12. Thus there is provided an annular space 79 which underlies the holes 78 provided in the filter support washer 77. After the filter washer 76 and the filter support washer 77 have been mounted within the annular recess 74, the spike assembly 16 can be secured permanently to the top of the drip chamber body 12 by suitable means such as ultrasonic welding. When this is the case, it can be seen the second flow passage 72 is in communication with the atmosphere through the annular recess 73 through the filter washer 76 through the openings 78 of the filter support washer through the annular space 79 which is in communication with the downwardly extending slots 28 provided in the upper outer portion of the wall 18 of the drip chamber body 12.

Finger-like tabs 81 are formed integral with the cap 56 on opposite sides of the same. The tabs facilitate insertion of the spike 61 as hereinafter described.

Operation and use of the universal drip chamber and spike assembly may now be briefly described as follows. Let it be assumed that it is desired to utilize the universal drip chamber and spike assembly 11 in conjunction with a controller and pump of the type described in co-pending application, Ser. No. 689115, filed May 24, 1976. Also, let it be assumed that the outlet tube 41 from the universal drip chamber and spike assembly 11 is connected to the inlet of the pump and that the outlet of the pump is connected to the patient. Also let it be assumed that the i.v. bottle to which the universal drip chamber and spike assembly 11 had been connected has run out of liquid and that the ball float 51 is seated within the valve seat formed by the annulus 47 to close off the outlet passage 38. As pointed out in co-pending application, Ser. No. 689,115, filed May 24, 1976, when this occurs an alarm will be initiated by the controller.

The universal drip chamber and spike assembly 11 is then removed from the i.v. bottle. A new i.v. bottle is placed on a table or stand with the stopper facing upwardly. The nurse or other attendant grasps the universal drip chamber and spike assembly 11 by the hand and presses it against the outwardly extending fingers 81 to force the central tip 64 of the spike into the permeable stopper in the bottle. The insertion is done rather carefully so that only the first step 62 will penetrate the stopper. As soon as the first step is in communication with the interior of the bottle, the bottle which is normally under a vacuum will be vented to the atmosphere through the passage 72 in a manner heretofore described. Any air entering through the bottle will be filtered by the hydrophobic filter 76. This occurrence can be ascertained when one hears a small hissing noise indicating that air is rushing into the i.v. bottle. As soon as the pressure within the interior of the bottle and the atmosphere has equalized, the universal drip chamber and spike assembly 11 can be forced inwardly until the second step is in communication with the interior of the bottle. As soon as this occurs, the flow passage 68 will be in communication with the liquid in the bottle. The bottle can then be taken and hung upside down on the hanger provided on the stand associated with the controller.

The drip chamber 14 is filled to a suitable level such as the level indicated by the line 21 with the liquid in the i.v. bottle. This is accomplished by using two fingers of the hand and grasping the upper portion of the drip chamber booth 13 and repeatedly compressing the same and then releasing it to cause a pumping action within the lower portion of the chamber 14 to cause liquid to enter the i.v. bottle and to flow into the chamber 14. This pumping action by the fingers is continued until the liquid level rises to the level of line 21. The liquid in the drip chamber 14 will thereafter remain at that level during operation of the drip chamber.

During the time that the drip chamber 14 is being filled to the level 21, the ball remains seated within the valve seat 46 because it is gripped by the annulus 47. As soon as the drip chamber has been filled to the desired level, the lower portion of the drip chamber booth 13 can be squeezed by hand as shown in FIG. 1. This compresses the valve seat around the ball-like member and causes the ball to be ejected from the valve seat and to float on the surface of the liquid in the drip chamber 14.

The pump of the controller can now be filled and placed in operation in the manner described in co-pending application, Ser. No. 689,115, filed May 24, 1976. During operation, the i.v. liquid as it is being utilized will drip through the drip chamber 14 so that it can be visually observed if desired. When the i.v. bottle again runs out of liquid, the level in the chamber 14 will drop until the ball comes into comtact with the seat 48. Because of the suction created by the pump, the ball 51 will be sucked into the valve seat to form a tight seal between the valve seat and the ball so that a vacuum condition will be created within the passage 38 to actuate an alarm which will call the nurse to insert a new i.v. bottle on the spike assembly 16 in the manner hereinfore described.

From the foregoing it can be seen that there has been provided a universal drip chamber and spike assembly which can be readily used. In addition to being capable of being used with bottles which require venting to the outside atmosphere, it also can be utilized with bottles which are self-venting or with collapsible type bottles. In the latter two cases, the spike 61 would be inserted rapidly into the stopper without the two-step procedure hereinbefore described for venting bottles of the rigid type which are not self-venting.

In addition, the universal drip chamber and spike assembly is constructed so that a new i.v. bottle can be placed on the spike without the necessity of disconnecting the needle from the patient and without danger of air being introduced into the veins of the patient. When air is introduced into the i.v. bottle through the spike assembly 11, it is carefully filtered in the manner hereinbefore described. The filter is also protected so that it will not be wetted by water and the like because of the constructon of the cap and its mounting over the filter and over the top end of the drip chamber body. Also as hereinbefore described, the steam 69 is constructed in such a manner so that the flow passage 68 is unobstructed at all times even when the ball is at the top of the drip chamber because of the recesses or cutouts 71 provided in the stem.

What is claimed is:

1. In a universal drip chamber and spike assembly for use with a source of liquid in a container having a neck with a permeable stopper disposed in the neck and for use with a tube connected to a patient, a drip chamber body defining the upper portion of a drip chamber, said body having a relatively rigid substantially transparent wall surrounding the upper portion of the drip chamber and being open at its lower end, a drip chamber booth formed of a flexible rubber-like material secured to the lower end of said drip chamber body and defining a lower portion of the drip chamber, said booth having an outlet flow passage in its lower extremity in communication with the drip chamber and adapted to be placed in communication with the tube connected to the patient and having means forming a valve seat in the drip chamber surrounding said outlet flow passage, said valve seat being in the form of an upstanding relatively thin self supporting annulus of a soft rubber-like material, a spike assembly mounted on the drip chamber body and being adapted to be inserted into the permeable stopper of the container to permit liquid to flow from the container into the drip chamber, said drip chamber being capable of receiving liquid from said container and a ball-like float member being capable of floating in said liquid in said drip chamber, said ball-like float member being of a size so that it is capable of seating within said annulus to a depth so that a major portion is disposed therein for closing off said outlet flow passage when substantially all of the liquid from the drip chamber has passed out of said drip chamber to form an air-tight seal between the ball-like member and said annulus to thereby prevent the flow of air from the drip chamber through the outlet flow passage, said booth having a sufficient length above the annulus when the ball-like float member is disposed in the annulus so that the booth can be squeezed by hand without dislodging the ball-like float member to pump liquid from the source into the drip chamber, said ball-like float member being retained by the annulus after it has seated in said annulus and after liquid has been pumped into the drip chamber to a level above the surface of the ball-like member, said booth being sufficiently compliant so that after the drip chamber has been filed to a desired level, it can be squeezed by hand to dislodge the ball-like float member from the annulus.

2. An assembly as in claim 1 wherein said spike has a first flow passage therein in communication with the drip chamber whereby when said spike is inserted into said stopper, liquid can pass from said bottle into said drip chamber, said spike being provided with first and second steps with said second step being closer to the outer end of said spike than said first step, said first flow passage opening through said first step, said spike assembly having a second flow passage formed therein and opening through said second step and being open to the atmosphere, hydrophobic filter means disposed in said second flow passage so that air passing from the atmosphere through said second flow passage must pass through the hydrophobic filter means.

3. An assembly as in claim 1 wherein said drip chamber booth is formed of a soft rubber having a durometer ranging from 25 to 30.

4. An assembly as in claim 1 wherein said booth is formed of a soft rubber-like material so that the portion of the booth in the vicinity of annulus can be squeezed to dislodge the ball from the annulus and wherein said annulus is formed of the same material as the booth.

5. In a universal drip chamber and spike assembly for use with a source of liquid in a container having a neck with a permeable stopper disposed in the neck and for use with a tube connected to a patient, a drip chamber body defining the upper portion of a drip chamber, said body having a relatively rigid substantially transparent wall surrounding the upper portion of the drip chamber and being open at its lower end, a drip chamber booth formed of a flexible rubber-like material secured to the lower end of said drip chamber body and defining the lower portion of the drip chamber, said booth having an outlet flow passage in its lower extremity in communication with the drip chamber and adapted to be placed in communication with the tube connected to the patient and having means forming a valve seat in the drip chamber surrounding said outlet flow passage, said valve seat being in the form of an upstanding relatively thin self supporting annulus of a soft rubber-like material, a spike assembly mounted on the drip chamber body and being adapted to be inserted into the permeable stopper of the container to permit liquid to flow from the container into the drip chamber, said drip chamber being capable of receiving liquid from said container and a ball-like float member capable of floating in said liquid in said drip chamber and being capable of engaging said valve seat for closing off said outlet flow passage when substantially al of the liquid from the drip chamber has passed out of said drip chamber to form an air-tight seal between the ball-like member and said valve seat to thereby prevent the flow of air from the drip chamber through the outlet flow passage, the booth being sufficiently compliant so that it can be squeezed by hand to dislodge the ball-like float member from the valve seat, said booth having a sufficient length above the valve seat when the ball-like member is disposed in the valve seat so that the booth can be squeezed by hand without dislodging the ball-like float member to pump liquid from the source into the drip chamber, said spike assembly having a spike with a first flow passage therein in communication with the drip chamber whereby when said spike is inserted into said stopper, liquid can pass from said bottle into said drip chamber, said spike being provided with first and second steps with said second step being closer to the outer end of said spike than said first step, said first flow passage opening through said first step, said spike assembly having a second flow passage formed therein and opening through said second step and being open to the atmosphere, hydrophobic filter means disposed in said second flow passage so that air passing from the atmosphere through said second flow passage must pass through the hydrophobic filter means, said drip chamber being provided with an upper wall and said spike being provided with a stem extending through said upper wall, said first flow passage in said spike extending through said stem into said drip chamber, said spike including a cap mounted over the top of said drip chamber body, said hydrophobic filter being disposed in said cap, said second flow passage in said spike being in communication with one side of the filter, the other side of the filter being in communication with the atmosphere.

6. A drip chamber assembly for use with the source of liquid to be supplied to a patient, means forming a drip chamber including a drip chamber booth formed of a flexible material with an inlet flow passage adapted to be connected to the source of liquid and an outlet passage adapted to be connected to the patient, the outlet passage beng formed in the drip chamber booth, a relatively thin self supporting annulus of flexible material formed in the booth and encircling said outlet flow passage to provide a valve seat and a ball-like float member disposed in said drip chamber being capable of floating in said liquid, said ball-like float member being of a size so that it is capable of seating within said annulus to a depth so that a major portion is disposed therein for closing off said outlet flow passage, said ball-like float member moving into said annulus when the liquid in the drip chamber is drained from the drip chamber to prevent the flow of air from the drip chamber through the outlet flow passage, said booth having a sufficient length above the annulus when the ball-like float member is disposed in the annulus so that the booth can be squeezed by hand without dislodging the ball-like float member to pump liquid from the source into the drip chamber, said ball-like float member being retained by the annulus after it has been seated in the annulus and after liquid has been pumped into the drip chamber to a level above the surface of the ball-like member, said booth being sufficiently compliant so that after the drip chamber has been filled to the desired level it can be squeezed by hand to dislode the ball-like float member from the annulus.

7. A universal drip chamber and spike assembly for use with source of i.v. liquid in a container having a neck with a permeable stopper disposed in the neck and for use with a tube connected to a patient, means forming a drip chamber, said means forming a drip chamber including an outlet flow passage adapted to be connected to said tube connected to the patient, a spike including a cap mounted on said means forming a drip chamber, first and second steps formed on the spike, said second step being closer to the outer end of the spike than said first step, said spike having formed therein a first flow passage extending through said first step and being in communication with the drip chamber, said spike having formed therein a second flow extending through said second step with the other end being open to the atmosphere and hydrophobic filer means mounted in the cap and disposed in said second flow passage so that air passing from the atmosphere into said second flow passage must pass through the hydrophobic filter means, said cap formed with a depending sidewall which extends below the filter means, said filter means lying in a plane perpendicular to the longitudinal axis of the drip chamber and having an area approximating that of the cross section of the drip chamber in a direction at right angles to the longitudinal axis of the drip chamber.

* * * * *